United States Patent [19]

Wang et al.

[11] Patent Number: 4,952,236

[45] Date of Patent: Aug. 28, 1990

[54] METHOD OF MAKING HIGH STRENGTH, LOW MODULUS, DUCTILE, BIOCOMPATIBLE TITANIUM ALLOY

[75] Inventors: Kathy K. Wang, Suffern, N.Y.; Larry J. Gustavson, Dover; John H. Dumbleton, Ridgewood, both of N.J.

[73] Assignee: Pfizer Hospital Products Group, Inc., New York, N.Y.

[21] Appl. No.: 357,494

[22] Filed: May 25, 1989

Related U.S. Application Data

[62] Division of Ser. No. 242,750, Sep. 9, 1988, Pat. No. 4,857,269.

[51] Int. Cl.$^5$ .............................................. C22B 4/00
[52] U.S. Cl. ...................................... 148/2; 75/10.26; 75/10.19; 148/421
[58] Field of Search ...................... 75/10.19, 10.26, 84, 75/65 EB

[56] References Cited

U.S. PATENT DOCUMENTS

| | | | |
|---|---|---|---|
| 3,024,102 | 3/1962 | Brown | 75/10.26 |
| 3,071,461 | 1/1963 | Schussler | 75/10.26 |
| 3,072,982 | 1/1963 | Gordon | 75/10.26 |
| 3,342,250 | 9/1967 | Treppschuh | 75/65 EB |
| 3,565,602 | 2/1971 | Konisi | 75/10.26 |
| 4,007,770 | 2/1977 | Timmons | 75/10.26 |
| 4,585,474 | 4/1986 | Andorfer | 75/10.26 |
| 4,681,627 | 7/1987 | Mae | 75/10.19 |
| 4,728,364 | 3/1988 | Bania | 75/10.26 |

*Primary Examiner*—Peter D. Rosenberg
*Attorney, Agent, or Firm*—Peter C. Richardson; Lawrence C. Akers; Mark Dryer

[57] ABSTRACT

Method for preparing a high strength, low modulus, ductile, biocompatible titanium base alloy containing one or more isomorphous beta stabilizers, eutectoid beta stabilizers and optional alpha stabilizers, characterized by a modulus of elasticity not exceeding 100 GPa; comprising blending pre-selected amounts of the alloying ingredients, melting the blend in a plasma arc furnace, allowing the melt to cool and solidify, vaccum arc remelting and thermomechanically processing the resulting solid to provide the desired alloy.

5 Claims, No Drawings

METHOD OF MAKING HIGH STRENGTH, LOW MODULUS, DUCTILE, BIOCOMPATIBLE TITANIUM ALLOY

This is a division, of application Ser. No. 242,750, filed Sept. 9, 1988 now U.S. Pat. No. 4,857,269.

BACKGROUND OF THE INVENTION

This invention relates to a biocompatible titanium base alloy characterized by high strength, low modulus and ductility, and to a method for the preparation of said alloy. The alloy of the invention is particularly suitable for the manufacture of prostheses and the invention also is concerned with a prosthesis made from the alloy.

Titanium base alloys for a variety of structural applications are known in the art and there are numerous patent and literature references disclosing a wide range of alloying elements which are used to provide alloys having desired characteristics, such as increased tensile strength and ductility. Generally, titanium and its alloys may exist in one or a mixture of two basic crystalline structures: the alpha phase, which is a hexagonal close-packed (HCP) structure, and the beta phase which is a body-centered cubic (BCC) structure. The transition temperature from the alpha to the beta phase is about 882° C. for pure titanium. Elements which promote higher transformation temperatures are known as alpha-stabilizers. Examples of alpha stabilizers are aluminum and lanthanum. Elements which promote lower transformation temperatures are known as beta-stabilizers. Beta stabilizers are classified in two groups: the isomorphous beta stabilizers, exemplified by molybdenum, niobium, tantalum, vanadium and zirconium; and the eutectoid beta stabilizers, exemplified by cobalt, chromium, iron, manganese and nickel. Thus, depending upon the type and amount of alloying elements, there are three general classes of titanium base alloy: alpha, alpha-beta and beta.

An example of a high strength titanium base alloy containing the beta stabilizers vanadium and iron and the alpha stabilizer aluminum is disclosed in U.S. Pat. No. 3,802,877. However, the biocompatibility of this alloy may be compromised because of the presence of vanadium, which should be avoided in an alloy used to fabricate an implant.

Bone implants made from titanium or titanium-containing alloys are known in the art. Implants, such as plates and screws, made from pure titanium were used in 1951 for the fixation of bone fractures when it was found by Jergesen and Leventhal that these implants exhibited good tissue tolerance. See Laing, P. G. "Clinical Experience with Prosthetic Materials," ASTM Special Technical Publication 684 (1979), pp. 203–4. However, although pure titanium has excellent corrosion resistance and tissue tolerance, its relative low strength, when compared to stainless steel, and unfavorable wear properties, limited its use for general bone implants.

In the 1970s pure titanium for surgical implants was replaced by an alloy containing aluminum and vanadium (Ti-6Al-4V) for the manufacture of high strength femoral prostheses. However, although no toxic reaction was reported in patients, the known toxicity of vanadium and the association of aluminum with various neurological disorders has raised considerable doubt about the safety of this alloy.

U.S. Pat. No. 4,040,129 discloses an implant for bone surgery and for dental therapeutics containing defined critical amounts of titanium and/or zirconium and other selected metallic elements including niobium, tantalum, chromium, molybdenum and aluminum. Alloying elements of questionable biocompatibility, such as vanadium, are specifically excluded.

In 1980 a Ti-5Al-2.5Fe alloy was disclosed for surgical implant application and in 1985 a Ti-6Al-7Nb alloy was disclosed for the manufacture of various types of femoral component stem. Each of these alloys contained a relatively high proportion of the suspect alloying element aluminum.

A biocompatible titanium base alloy suitable for bone implants should meet at least the following requirements:

1. Potentially toxic elements, such as vanadium, copper and tin, should be avoided completely.
2. Elements which may have potential toxicological problems, such as chromium, nickel and aluminum should be used only in minimal, acceptable amounts.
3. The alloy should have high corrosion resistance.
4. The alloy should have at least the following desired mechanical properties: flow modulus, high strength and good smooth and notched fatigue strength.
5. The alloy should have good workability and ductility.

It has now been found that a biocompatible alloy meeting the desired requirements and, in particular, having a combination of high strength and low modulus desirable for orthopaedics but not possessed by any alloy disclosed in the prior art, may be produced, preferably by double plasma melting, from a carefully balanced formulation of beta stabilizers, alpha stabilizers and titanium.

Thus commonly assigned U.S. Pat. No. 4,857,269 provides a high strength, low modulus, ductile, biocompatible titanium base alloy consisting essentially of the following alloying components:

an amount up to 24% by weight of at least one isomorphous beta stabilizer selected from the group consisting of molybdenum, tantalum, niobium and zirconium, provided that molybdenum, when present, is in an amount of at least 10% by weight, and when molybdenum is present with zirconium the molybdenum is an amount of 10 to 13% by weight and the zirconium is in an amount of 5 to 7% by weight;

an amount up to 3.0% by weight of at least one eutectoid beta stabilizer selected from the group consisting of iron, manganese, chromium, cobalt and nickel;

optionally an amount up to 3.0% by weight of at least one metallic alpha stabilizer selected from the group consisting of aluminum and lanthanum;

and the balance titanium, apart from incidental impurities, but not exceeding by weight, among the non-metallic alpha stabilizers, 0.05% carbon, 0.30% oxygen and 0.02%, nitrogen, and not exceeding 0.02% of the eutectoid former hydrogen; the proportion of each of the alloying components being balanced to provide an alloy having a modulus of elasticity not exceeding 100 GPa.

A preferred embodiment of the above alloy is an alloy having a modulus of elasticity of 66.9 to 100 GPa; a 0.2% offset yield strength of 925 to 1221 MPa; a rotating beam fatigue strength of 483 to 621 MPa at 107 cycles and of 345 to 380 MPa at a stress concentration factor, $K_t$, of 1.6; and a tensile elongation of at least 10%.

SUMMARY OF THE INVENTION

The present invention provides a method for preparing a high strength, low modulus, ductile, biocompatible titanium base alloy which comprises mechanically blending particles of the following alloying components:

- up to 24% by weight of at least one isomorphous beta stabilizer selected from the group consisting of molybdenum, tantalum, niobium and zirconium;
- up to 3.0% by weight of at least one eutectoid beta stabilizer selected from the group consisting of iron, manganese, chromium, cobalt and nickel;
- optionally up to 3.0% by weight of at least one metallic alpha stabilizer selected from the group consisting of aluminum and lanthanum;
- and the balance titanium;
- introducing the resulting blended feedstock into a plasma arc furnace wherein the blend is melted to form a homogenous melt, allowing the melt to cool and solidify, vacuum arc remelting the resulting solid to assure that the hydrogen content does not exceed 0.02% by weight and thermomechanically processing the resulting solid at a temperature within the range of 710° to 1038° C. to provide an alloy having a modulus elasticity not exceeding 100 GPa.

The term "thermomechanically processing" is a term of art and is well understood in the art to include such procedures as forging, hot rolling and surface conditioning, each of said procedures comprising a thermal, i.e. elevated temperature, and a mechanical component. As used herein the term is intended to have its conventional meaning and includes the aforesaid procedures, which procedures are performed during the preparation of the desired alloy, as hereinafter described, until the desired characteristics are achieved.

A preferred alloy prepared by the method of the invention is an alloy consisting essentially of 10 to 13% by weight of molybdenum; 5 to 7% by weight of zirconium; 0.2 to 3.0% by weight of iron; 0 to 3.0% by weight of aluminum; and the balance titanium, apart from incidental impurities.

A particularly preferred embodiment is an alloy consisting essentially of about 11.5% by weight molybdenum, about 6.0% by weight zirconium; about 0.4 to about 2.0% by weight iron, 0 to about 1.0% by weight aluminum; and the balance titanium, apart from incidental impurities.

Another preferred embodiment is an alloy consisting essentially of 10.0 to 20.0% by weight niobium; 1.0 to 4.0% by weight zirconium; about 2.0% by weight iron; up to 1.0% by weight aluminum; and the balance titanium, apart from incidental impurities.

An alloy conforming to any of the above compositions and exhibiting the described properties is particularly suitable for use in bone implants or prostheses and, accordingly, the present invention additionally provides a prosthesis made from a high strength, low modulus, ductile, biocompatible titanium base alloy as described above.

DETAILED DESCRIPTION OF THE INVENTION

The present invention provides a titanium base alloy which possesses not only the corrosion resistance and tissue tolerance of pure titanium and the high strength of previously disclosed titanium alloys but also the low modulus, ductility and improved notch resistance required for an improved biocompatible alloy as described above.

To achieve the desired properties and avoid the use of potentially toxic elements, such as vanadium and tin, and minimize the use of suspect elements, such as aluminum, alloys were made from titanium with varying amounts of the isomorphous beta stabilizers molybdenum, tantalum, niobium and zirconium; the eutectoid beta stabilizers iron, manganese, chromium, cobalt and nickel, preferably iron; and, optionally, tolerable amounts of the alpha stabilizers, aluminum and lanthanum. The alloys were preferably made by mechanically blending accurately weighed portions of the pure elements melting the blend in a plasma arc furnace and remelting as necessary, preferably in a vacuum arc furnace, to achieve uniformity. The alloys were then thermomechanically processed to provide products having the desired properties.

The following description illustrates the production of allows according to the invention (the present alloys) as well as other alloys made for comparative purposes to emphasize the advantageous properties of the present alloys.

A preliminary batch of alloys (Examples 1–6) was produced and processed in accordance with the following procedure:

Accurately weighed portions of the pure elements: titanium, molybdenum, zirconium and iron (Examples 1 to 3) and also aluminum (Examples 4 to 6) were introduced as starting materials into a vacuum arc furnace where they were melted into 100 gram buttons. Each button was remelted 4–5 times to ensure its chemical uniformity.

The six buttons were first flattened by forging at 1010° C. and then hot rolled unidirectionally at 972° C. from 1.23 cm to 0.52 cm. in thickness with approximately 10% reduction per pass. Each rolled plate was surface conditioned after the rolling at 927° C. The plates were finally rolled at 760° C. with additional 53% reduction to a final sheet having a thickness of approximately 0.244 cm.

The composition of each alloy prepared by the above procedure is set out in the following Table I:

TABLE I

| Example No. | Mo | Zr | Fe | Al | Sn | C* | N* | O** | H* | Ti |
|---|---|---|---|---|---|---|---|---|---|---|
| 1 | 11.5 | 6.0 | 0.2* | — | — | 0.05 | 0.02 | 0.15 | 0.02 | Bal |
| 2 | 11.5 | 6.0 | 2.0 | — | — | 0.05 | 0.02 | 0.15 | 0.02 | Bal |
| 3 | 11.5 | 6.0 | 0.4 | — | — | 0.05 | 0.02 | 0.15 | 0.02 | Bal |
| 4 | 11.5 | 6.0 | 0.2* | 1.0 | — | 0.05 | 0.02 | 0.14 | 0.02 | Bal |
| 5 | 11.5 | 6.0 | 2.0 | 1.0 | — | 0.05 | 0.02 | 0.15 | 0.02 | Bal |
| 6 | 11.5 | 6.0 | 0.4 | 1.0 | — | 0.05 | 0.02 | 0.11 | 0.02 | Bal |

*maximum estimated content; full analysis not made.
**average of two analyses, to two decimal places.

Specimens of the above alloys were prepared for optical metallographic inspection by grinding on successively finer silicon carbide papers through 800 grit, and the specimens were then polished. The specimens were then treated with an etching solution comprising 5–6 drops of hydrofluoric acid, 30 ml. nitric acid and 68 ml. water. The microstructure of the as rolled and solution treated (718°–774° C. with an inert gas fan cool (GFC)) specimens was observed after etching.

The above metallographic study revealed that the specimen alloys with 2% iron (Examples 2 and 5) exhibit completely recrystallized structures with well defined grain boundaries and little primary alpha phase after solution treatment at 718° C. Beta transus study indicated that the additions of iron lowered the beta transus temperature. For example, unrecrystallized grain structures were still found in the alloys of Examples 1 and 4 after solution treatment at 774° C.

In order to test the corrosion resistance of the alloy specimens, anodic polarization tests were conducted on the solution treated sheets. The specimens were in the form of discs having a diameter of 1.6 cm. and a thickness of 0.3 cm. Each disc was finished to 600 grit immediately before testing. The test environment was a 0.9% deaerated solution of sodium chloride at a temperature of 37° C.

No significant difference in the corrosion behavior was found between the specimen alloys and the known Ti-6Al-4V alloy.

The solution treated titanium alloy specimens were subjected to microhardness tests. The effects of solution treatment on the hardness of titanium alloy sheet are set out in the following Table II:

TABLE II

| Example No. | Rockwell Hardness (Rc) of Titanium Alloys | | | | |
|---|---|---|---|---|---|
| | Solution Treatment Temperature | | | | |
| | 718° C. | 732° C. | 746° C. | 760° C. | 774° C. |
| 1 | 37.5 | 38.5 | 37 | 38 | 37 |
| 2 | 31 | 30 | 31 | 32 | 33 |
| 3 | 35 | 36 | 37.5 | 37.5 | 37.5 |
| 4 | 26 | 24 | 24 | 24 | 27 |
| 5 | 28 | 29 | 29 | 30 | 31 |
| 6 | 28.5 | 28 | 31 | 28.5 | 28.5 |

It is apparent from the above results that the alloys containing no aluminum, Examples 1, 2 and 3, are much harder than those containing 1% aluminum. No significant hardness changes were found between the 718° C. and 774° C. solution treatments. Room temperature tensile tests were conducted on the solution treated titanium alloy sheets. An extensometer was used to measure the elastic modulus of these alloys. The tensile test results are set out in the following Table III:

TABLE III

| | Room Temperature Tensile Properties** | | | |
|---|---|---|---|---|
| | 718° C. Solution Treated | | | |
| Example No. | E GPa | UTS MPa | YS MPa | El (%) |
| 1 | 98.7 | 1162 | 1138 | 3.0 |
| 2 | 88.3 | 1156 | 1134 | 13.1 |
| 3 | 75.9 | 1186 | 1147 | 7.7 |
| 4 | 66.9 | 1014 | 977 | 8.6 |
| 5 | 66.9 | 1069 | 1029 | 14.2 |
| 6 | 74.5 | 1048 | 991 | 6.8 |

**Average of two tests.

The results in Table III show that Ti-Mo-Zr alloys with 1% Al addition have the desired low modulus and high strength, and with 2% Fe addition have significantly improved ductility. The alloy of Example 5, which exhibits low modulus, high strength and good ductility, is particularly promising.

For comparative purposes the tensile properties of the known Ti-6Al-4V alloy are given below:

| | E GPa | UTS MPa | YS MPa | El (%) |
|---|---|---|---|---|
| Ti—6Al—4V | 110 | 931 | 845 | 15 |

A further batch of alloys (Examples 7 to 12) having similar molybdenum and zirconium contents to those of Examples 1 to 6, was produced and processed in accordance with the following procedure: Six 7.6 cm diameter ingots having the composition set out in Table IV hereinbelow were produced by double plasma melting.

TABLE IV

| Example No. | Mo | Zr | Fe | Al | C* | N* | O* | H* | Ti |
|---|---|---|---|---|---|---|---|---|---|
| 7 | 11.5 | 6 | 2.0 | — | 0.05 | 0.02 | 0.25 | 0.02 | Bal |
| 8 | 11.5 | 6 | 2.0 | 0.5 | 0.05 | 0.02 | 0.25 | 0.02 | Bal |
| 9 | 11.6 | 6 | 2.0 | 1.0 | 0.05 | 0.02 | 0.25 | 0.02 | Bal |
| 10 | 11.5 | 6 | 0.4 | — | 0.05 | 0.02 | 0.25 | 0.02 | Bal |
| 11 | 11.5 | 6 | 0.4 | 0.5 | 0.05 | 0.02 | 0.25 | 0.02 | Bal |
| 12 | 11.5 | 6 | 0.4 | 1.0 | 0.05 | 0.02 | 0.25 | 0.02 | Bal |

*Maximum estimated content

The starting feed used to form the ingots was in the form of a cold compact comprising a uniform blend of pure elements: titanium, molybdenum, zirconium and iron (Examples 7 and 10) and also aluminum (Examples 8, 9, 11 and 12). The plasma melted ingots were then vacuum arc melted to produce 11.4 cm. diameter ingots.

The vacuum arc melted ingots were then forged into 3.8 cm. bars at 954°–1038° C. Each forged bar was cut into three sections and hot rolled at three different temperatures, 732°, 760° and 788° C. after preheat for 45 minutes at the rolling temperature. Samples taken from four different locations in each forged bar were used for chemical analysis and the resulting analysis showed the composition to be substantially uniform along the length of the bar.

Metallographic examination was conducted on the rolled bars in eight different conditions, viz: as rolled; 718° C./GFC; 718° C./AC; 718° C./WQ; 732° C./GFC; 732° C./WQ, and 732° C./AC and 774° C./GFC. The metallographic preparation of specimens was the same as that described above for Examples 1–6.

The metallographic examination revealed that the beta transus temperature of the alloy containing 2% iron (718° C.) is lower than that of the alloy containing 0.4% iron (732° C.). The addition of aluminum tended to raise the beta transus temperature only in the alloy containing 0.4% iron. For example, the alloy of Example 12 has a beta transus temperature of 774° C.

Microhardness was checked on the rolled and solution treated bar samples. The hardness of the rolled bar samples is comparable to that of the sheet samples of Examples 1 to 6. The results are shown in the following Table V.

TABLE V

| | Bar Stock Rolling Temperature | | |
|---|---|---|---|
| Example No. | 732° C. | 760° C. | 788° C. |
| Rockwell Hardness (Rc) of 718° C. S.T./GFC Alloys | | | |
| 7 | 31 | 29 | 30–31 |
| 8 | 28–29 | 29 | 27 |
| 9 | 28–29 | 27–28 | 26–27 |
| 10 | 36 | 38–39 | 35–36 |
| 11 | 33 | 32–33 | 34 |
| 12 | 29 | 27–28 | 28–29 |

TABLE V-continued

| Example No. | Bar Stock Rolling Temperature | | |
|---|---|---|---|
| | 732° C. | 760° C. | 788° C. |
| Rockwell Hardness (Rc) of 718° C. S.T./WQ Alloys | | | |
| 7 | 31 | 33 | 30 |
| 8 | 31 | 28 | 29 |
| 9 | 28–29 | 29 | 27 |
| 10 | 25–26 | 23–25 | 23–24 |
| 11 | 27 | 24 | 22–23 |
| 12 | 29.5 | 27–28.5 | 27 |

The effects of cooling rate after solution treatment on the hardness of the above alloys are shown in the following Table VI.

TABLE VI

| Example No. | Rolling Temperature | Rockwell Hardness (Rc) | | |
|---|---|---|---|---|
| | | 718° C./GFC | 718° C./AC | 718° C./WQ |
| 7 | 732° C. | 31 | 31 | 31 |
| | 760° C. | 29 | 33 | 33 |
| | 788° C. | 30–31 | 31 | 30 |
| 8 | 732° C. | 28–29 | 28–29 | 31 |
| | 760° C. | 29 | 30.5 | 28 |
| | 788° C. | 27 | 28 | 29 |
| 9 | 732° C. | 26–27 | — | 27 |
| | 760° C. | 27–28 | — | 29 |
| | 788° C. | 28–29 | — | 28–29 |
| 10 | 732° C. | 36 | 32 | 25–26 |
| | 760° C. | 38–39 | 39 | 23–25 |
| | 788° C. | 35–36 | 38–39 | 23–24 |
| 11 | 732° C. | 33 | 28 | 27 |
| | 760° C. | 32–33 | 36 | 24 |
| | 788° C. | 34 | 35 | 22–23 |
| 12 | 732° C. | 29 | 30 | 29.5 |
| | 760° C. | 27–28 | 32 | 27–28.5 |
| | 788° C. | 28–29 | 31–32 | 27 |

The results in Table VI indicate that the cooling rate does not significantly affect the hardness of the alloys containing 2% iron or 1% aluminum. The presence of 2% iron (stabilizing beta matrix) and aluminum (forming alpha phase) can suppress the athermal omega formation.

Room temperature tensile tests were conducted on the solution treated bars. An extensometer was attached to the tensile bar to measure the elastic modulus of these alloys. Room temperature tensile properties of the rolled bars are shown in the following Tables VII, VIII and IX. Three different rolling temperatures and solution treatments are presented. The tensile properties of these alloys are not significantly affected by the rolling temperatures between 788° C. and 732° C. The presence of 2% iron and up to 1% aluminum improves ductility and modulus, respectively. The preferred rolling and annealing temperatures are 732°–760° C. and 718° C., respectively, with an inert gas fan cool (GFC) found to be sufficient cooling rate following annealing to prevent loss of ductility due to omega formation.

TABLE VII

| Alloy Composition | 732° C. Rolled Bar | | | | | |
|---|---|---|---|---|---|---|
| | Example No. | | | | | |
| | 7 | 8 | 9 | 10 | 11 | 12 |
| 718° C./GFC | | | | | | |
| E(GPa) | 87.6 | 78.7 | 82.1 | 97.3 | 77.3 | 82.1 |
| U.T.S.(MPa) | 1103 | 1028 | 1102 | 1217 | 1020 | 1136 |
| Y.S.(MPa) | 1098 | 1018 | 1089 | 1217 | 927 | 1103 |
| EL(%) | 20.0 | 20.3 | 18.8 | 12.1 | 15.1 | 11.8 |
| RA(%) | 56.3 | 59.2 | 42.4 | 43.9 | 51.1 | 38.2 |
| 718° C./WQ | | | | | | |
| E(GPa) | 85.6 | 85.6 | — | 82.8 | 80.7 | 84.9 |
| U.T.S.(MPa) | 1134 | 1100 | — | 1065 | 989 | 1083 |
| Y.S.(MPa) | 1120 | 1074 | — | 1035 | 944 | 1045 |
| EL(%) | 16.6 | 17.8 | — | 13.7 | 15.4 | 16.9 |
| RA(%) | 38.9 | 41.4 | — | 51.6 | 56.6 | 49.9 |
| 732° C./WQ | | | | | | |
| E(GPa) | 87.6 | 84.9 | — | 87.6 | 92.5 | 91.1 |
| U.T.S.(MPa) | 1148 | 1125 | — | 1121 | 1161 | 1108 |
| Y.S.(MPa) | 1137 | 1094 | — | 1105 | 1161 | 1055 |
| EL(%) | 17.9 | 16.3 | — | 8.6 | 13.1 | 15.7 |
| RA(%) | 43.1 | 39.7 | — | 42.4 | 43.7 | 48.6 |

Note: Each of the above figures is the average of two tests. The alloy of Example 9 solution treated at 718° C./WQ and 732° C./WQ was not tested.

TABLE VIII

| Alloy Composition | 760° C. Rolled Bar | | | | | |
|---|---|---|---|---|---|---|
| | Example No. | | | | | |
| | 7 | 8 | 9 | 10 | 11 | 12 |
| 718° C./GFC | | | | | | |
| E(GPa) | 86.3 | 78.7 | 79.4 | 97.3 | 81.4 | 81.4 |
| U.T.S.(MPa) | 1141 | 989 | 1007 | 1228 | 1145 | 1112 |
| Y.S.(MPa) | 1140 | 985 | 994 | 1224 | 1145 | 1085 |
| EL(%) | 18.0 | 23.4 | 20.8 | 13.4 | 11.1 | 13.3 |
| RA(%) | 42.4 | 71.4 | 52.6 | 45.9 | 39.8 | 38.1 |
| 718° C./WQ | | | | | | |
| E(GPa) | 87.6 | 91.1 | — | 87.6 | 86.9 | 88.3 |
| U.T.S.(MPa) | 989 | 1113 | — | 1069 | 1000 | 1079 |
| Y.S.(MPa) | 1143 | 1063 | — | 1034 | 919 | 1023 |
| EL(%) | 15.3 | 17.1 | — | 14.2 | 17.8 | 16.6 |
| RA(%) | 36.0 | 43.0 | — | 45.4 | 57.0 | 52.7 |
| 732° C./WQ | | | | | | |
| E(GPa) | 87.6 | 84.9 | — | 93.8 | 82.1 | 89.7 |
| U.T.S.(MPa) | 1166 | 1063 | — | 1154 | 1007 | 1063 |
| Y.S.(MPa) | 1129 | 1042 | — | 1142 | 936 | 1012 |
| EL(%) | 15.4 | 19.4 | — | 8.8 | 16.0 | 15.6 |
| RA(%) | 34.4 | 52.1 | — | 35.7 | 54.6 | 48.9 |

Note: Each of the above figures is the average of two tests.

TABLE IX

| Alloy Composition | 788° C. Rolled Bar | | | |
|---|---|---|---|---|
| | Example No. | | | |
| | 7 | 9 | 11 | 12 |
| 718° C./GFC | | | | |
| E (GPa) | 83.5 | 82.1 | 83.5 | 79.4 |
| U.T.S. (MPa) | 1107 | 970 | 1181 | 1116 |
| Y.S. (MPa) | 1100 | 958 | 1161 | 1085 |
| EL(%) | 16.8 | 23.4 | 10.7 | 12.6 |
| RA(%) | 60.3 | 66.6 | 28.4 | 38.0 |
| 718° C./WQ | | | | |
| E (GPa) | 87.6 | — | 93.8 | 87.6 |
| U.T.S. (MPa) | 1136 | — | 1140 | 1053 |
| Y.S. (MPa) | 1098 | — | 1086 | 985 |
| EL(%) | 16.7 | — | 14.5 | 17.1 |
| RA(%) | 41.7 | — | 44.4 | 54.1 |
| 732° C./WQ | | | | |
| E (GPa) | 89.1 | — | 82.8 | 84.9 |
| U.T.S. (MPa) | 1105 | — | 1128 | 1045 |
| Y.S. (MPa) | 1091 | — | 1088 | 972 |
| EL(%) | 16.1 | — | 13.7 | 17.6 |
| RA(%) | 40.1 | — | 30.8 | 52.9 |

Note:
Each of the above figures is the average of two tests. The alloys of Examples 8 and 10 were not tested in this program.

The modulus of elasticity (E) of the alloys of Examples 8, 9 and 12 was determined by dynamic modulus testing. The test samples rolled at 760° C. and solution treated at 718° C./GFC were tested in a Magnaflux Type FM-500 Elastomat to determine their resonant frequency. The modulus of elasticity (E) was then calculated from the equation:

TABLE IX

Tensile Properties of Ti—Nb—Fe Rolled Bars

| Example No. | Alloy Composition | Rolling Temperature | E (GPa) | U.T.S. (MPa) | Y.S. (MPa) | El. (%) | RA (%) | Remarks |
|---|---|---|---|---|---|---|---|---|
| 13. | Ti—10Nb—2Fe | 732° C. | 94.5 | 1237 | 1096 | 11.4 | 38.4 | (1) |
| 14. | Ti—10Nb—2Fe—1Zr | 760° C. | 92.5 | 1314 | 1221 | 9.0 | 32.5 | (1) |
|  |  | 732° C. | 93.8 | 1119 | 1073 | 12.9 | 54.0 | (1) |
| 15. | Ti—10Nb—2Fe—4Zr | 760° C. | 80.0 | 978 | 852 | 12.3 | 36.5 | (2) |
|  |  | 732° C. | 87.6 | 1072 | 906 | 16.2 | 55.2 | (2) |
|  |  | 732° C. | 94.5 | 989 | 858 | 13.6 | 33.9 | (3) |
| 16. | Ti—15Nb—2Fe | 788° C. | 86.9 | 1176 | 1010 | 8.1 | 22.6 | (1) |
|  |  | 788° C. | 99.4 | 1036 | 952 | 11.0 | 36.3 | (3) |
|  |  | 760° C. | 82.8 | 1179 | 1034 | 7.9 | 16.8 | (1) |
|  |  | 760° C. | 94.5 | 1085 | 981 | 10.0 | 30.1 | (3) |
|  |  | 732° C. | 84.2 | 1179 | 1134 | 7.9 | 21.8 | (3) |
| 17. | Ti—15Nb—2Fe—1Zr | 760° C. | 98.7 | 1143 | (a) | (a) | (a) | (1) |
|  |  | 732° C. | 95.2 | 1345 | (a) | (a) | (a) | (1) |
| 18. | Ti—15Nb—2Fe—4Zr | 788° C. | 86.2 | 1224 | 1053 | 8.1 | 23.3 | (1) |
| 19. | Ti—20Nb—2Fe—1Zr | 760° C. | 92.5 | 1006 | 885 | 14.2 | 24.8 | (3) |
|  |  | 732° C. | 86.9 | 1092 | 1041 | 8.5 | 25.1 | (3) |

(a) Specimen failed near radius or in thread area before yield point was obtained.
(1) Samples were solution treated at 718° C. with an inert gas fan cool.
(2) Samples were treated at 774° C. with an inert gas fan cool.
(3) Samples were solution treated at 732° C. with water quench.
Note: Each of the above figures is the average of two tests.

$$E = 4.0015 \times 10^{-4} DL^2 fR^2$$

Where E is in GPa, D is density of g/cm$^3$, L is length in cm, fR is resonant frequency in hertz.

Results show that the modulus of elasticity calculated from resonant frequency is comparable to that determined from tensile testing.

The results in Tables VII, VIII and IX show that the alloys tested have the desired low modulus and high strength required for bone implants.

Room temperature rotating beam fatigue tests were conducted on the rolled bars solution treated at 718° C./GFC. Table X presents the smooth and notched fatigue properties of the rolled bars of Examples 7, 8, 9, 11 and 12. Fatigue data of Ti-6Al-4V were also included in table X for comparison. Results indicate that the smooth fatigue strength of each of the alloys tested is comparable to that of Ti-6Al-4V. The notched fatigue strength of the alloys tested is much higher than that of Ti-6Al-4V. It was found that the fatigue strength of the alloys containing no aluminum is significantly influenced by the final rolling temperature. For example, the alloy of Example No. 7 rolled at 732° C. has a fatigue strength of 590 MPa. The fatigue strength is reduced to 485 MPa when the alloy of Example 7 was rolled at 788° C.

TABLE X

Rotating Beam Fatigue Strength at 10$^7$ Cycles (MPa)

| Example No. | Smooth | Notched (Kt = 1.6) |
|---|---|---|
| 7 | 485–590 | 345 |
| 8 | 485–520 | 345 |
| 9 | 550–590 | —(1) |
| 10 | —(1) | —(1) |
| 11 | 590–620 | 345 |
| 12 | 590–620 | 400 |
| Ti—6Al—4V | 580 | 276 |

(1)Alloys were not tested in this program.

The following Examples illustrate a series of alloys according to the invention in which the isomorphous beta stabilizer molybdenum is replaced by niobium. The alloys were prepared in a manner similar to those of the preceding Examples. The compositions and mechanical properties of the alloys are set out in Table XI.

The alloys of Examples 13 to 19 exhibited the desired low modulus and high strength. The lower than expected elongation may be due to the high carbon and oxygen contents in these alloys. The corrosion resistance of these Ti-Nb-Fe alloys were found to be as good as the Ti-Mo-Zr-Fe alloys and the Ti-6Al-4V alloy.

Only the alloy of Example 15 was fatigue tested, because it has a particularly low modulus (80 GPa). The smooth and notched fatigue properties of the alloy of Example 15 are given in Table XII. The data indicate that the alloy of Example 15 exhibits good smooth and excellent notched fatigue strength for bone implants

TABLE XII

Rotating Beam Fatigue Properties at 10$^7$ cycles (MPa)

| Example | Smooth | Notched (Kt = 1.6) |
|---|---|---|
| 15 | 485 | 380 |

We claim:

1. A method for preparing a high strength, low modulus, ductile titanium base alloy which comprises mechanically blending particles of the following alloying components:

up to 24% by weight of at least one isomorphous beta stabilizer selected from the group consisting of molybdenum, tantalum, niobium and zirconium;

up to 3.0% by weight of at least one eutectoid beta stabilizer selected from the group consisting of iron, manganese, chromium, cobalt and nickel;

optionally up to 3.0% by weight of at least one metallic alpha stabilizer selected from the group consisting of aluminum and lanthanum;

and the balance titanium;

introducing the resulting blended feedstock into a plasma arc furnace wherein the blend is melted to form a homogenous melt, allowing the melt to cool and solidify, vacuum arc remelting the resulting solid to assure that the hydrogen content does not exceed 0.02% by weight and thermomechanically processing the resulting solid at a temperature within the range of 710° to 1038° C. to provide an alloy having a modulus of elasticity not exceeding 100 GPa.

2. A method according to claim 1, in which the resulting alloy has a modulus of elasticity of 66.9 to 100 GPa; a 0.2% offset yield strength of 925 to 1221 MPa: a rotating beam fatigue strength of 483 to 621 MPa at $10^7$ cycles and of 345 to 380 MPa at a stress concentration factor, $k_t$, of 1.6; and a tensile elongation of at least 10%.

3. A method according to claim 1, in which the metal ingredients of the feedstock comprise 10 to 13% by weight molybdenum; 5 to 7% by weight zirconium; 0.2 to 3.0% by weight iron; 0 to 3.0% by weight aluminum; and the balance titanium.

4. A method according to claim 2, in which the metal ingredients of the feedstock comprise about 11.5% by weight molybdenum, about 6.0% by weight zirconium, about 0.4 to about 2.0% by weight iron, 0 to about 1.0% by weight aluminum and the balance titanium.

5. A method according to claim 1, in which the metal ingredients of the feedstock comprise 10.0 to 20.0% by weight niobium; 1.0 to 4.0% by weight zirconium; about 2.0% by weight iron: up to 1.0% by weight aluminum; and the balance titanium.

* * * * *